(12) United States Patent
Shim et al.

(10) Patent No.: US 7,985,453 B2
(45) Date of Patent: Jul. 26, 2011

(54) APPARATUS FOR CALIBRATING OPTICAL SCANNER, METHOD OF MANUFACTURING THE SAME, AND METHOD OF CALIBRATING OPTICAL SCANNER USING THE SAME

(75) Inventors: Jeo-young Shim, Yongin-si (KR); Sung-ouk Jung, Suwon-si (KR); Jin-na Namgoong, Yongin-si (KR); Kyu-tae Yoo, Seoul (KR); Jang-seok Ma, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 12/709,741

(22) Filed: Feb. 22, 2010

(65) Prior Publication Data

US 2010/0183812 A1    Jul. 22, 2010

Related U.S. Application Data

(62) Division of application No. 11/338,994, filed on Jan. 25, 2006, now Pat. No. 7,727,622.

(30) Foreign Application Priority Data

Jan. 25, 2005   (KR) ................. 10-2005-0006576

(51) Int. Cl.
*B05D 5/00* (2006.01)
*B05D 1/36* (2006.01)
*G01N 21/47* (2006.01)

(52) U.S. Cl. ..................... 427/337; 427/407.1
(58) Field of Classification Search ................. 427/299, 427/337, 407.1, 2.13, 157, 162, 301, 333, 427/399
See application file for complete search history.

(56) References Cited

U.S. PATENT DOCUMENTS

| | | | |
|---|---|---|---|
| 3,612,866 A | 10/1971 | Stevens | |
| 5,464,960 A | 11/1995 | Hall et al. | |
| 5,585,639 A | 12/1996 | Dorsel et al. | |
| 5,639,671 A * | 6/1997 | Bogart et al. | 436/518 |
| 5,772,656 A | 6/1998 | Klopotek | |
| 6,258,593 B1 | 7/2001 | Schembri et al. | |
| 6,794,424 B2 | 9/2004 | Holcomb et al. | |

FOREIGN PATENT DOCUMENTS

| | | |
|---|---|---|
| FR | 2 848 670 A1 | 6/2004 |
| JP | 11-352299 A | 12/1999 |
| JP | 3093851 U | 2/2003 |
| KR | 1020040093679 A | 11/2004 |

OTHER PUBLICATIONS

Gao et al., "Monomolecular Layers of Pyrene as a Sensor to Dicarboxylic Acids," J. Phys. Chem. B 2004, 108, 1207-1213.*
Fang et al., "Synthesis and solvent-sensitive fluorescence properties of a novel surfcae-functionalized chitosan film: potential materials for reversible information storage," Journal of Photochemistry and Photobiology A: Chemistry 135 (2000) 141-145.*
Katoh et al., "Polymer-bound n-hydroxysuccinimide esters: a column-free fluorescent-labeling method," Bioorganic & Medicinal Chemistry Letters 9 (1999) 881-884.*
Korean Office Action with English Translation for Application No. 10-2005-0006576 dated Jun. 7, 2006.
Partial European Search Report for Application No. 05027638.5-2204 dated Jun. 22, 2006.
Extended European Search Report for Application No. 05027638.5-2204 dated Dec. 18, 2006.
Chinese Office Action with English Translation for Application No. 2006100058686 dated Jul. 25, 2008.
Fluorescence properties of immobilized pyrene on quartz surface; Hui Wang, et al.; Materials Chemistry and Physics 77 (2002) 185-191.
Polymer-Bound N-Hydroxysuccinimide Esters: A Column-Free Fluorescent-Labeling Method; Miho Katoh, et al.; Bioorganic & Medicinal Chemistry Letters 9 (1999) 881-884.
Novel Molecular Optical Memory of Luminescent Langmuir-Blodgett Films; XP 000099682; Masamichi Fujihira, et al.; 0040-6090 89; Jun. 7, 1989, pp. 485-492.
Synthesis and solvent-sensitive fluorescence properties of a novel surface-functionalized chitosan film: potential materials for reversible information storage; Yu Fang, et al.; Journal of Photochemistry and Photobiology A: Chemistry 135 (2000) 141-145.
Monomolecular Layers of Pyrene as a Sensor to Dicarboxylic Acids; Lining Gae, et al.; XP-002383664; J. Phys. Chem B 2004, 108, 1207-1213.

* cited by examiner

*Primary Examiner* — William Phillip Fletcher, III
(74) *Attorney, Agent, or Firm* — Cantor Colburn LLP

(57) ABSTRACT

A method of manufacturing a calibration apparatus for an optical scanner. The method includes reacting a substrate coated with a functional group and a molecule capable of forming an activated excimer to immobilize the molecule on the substrate.

4 Claims, 3 Drawing Sheets

APPARATUS FOR CALIBRATING OPTICAL SCANNER, METHOD OF MANUFACTURING THE SAME, AND METHOD OF CALIBRATING OPTICAL SCANNER USING THE SAME

CROSS-REFERENCE TO RELATED PATENT APPLICATION

This application is a divisional of U.S. patent application Ser. No. 11/338,994, filed on Jan. 25, 2006, and issued as U.S. Pat No. 7,727,622 which claims priority to Korean Patent Application No. 10-2005-0006576, filed on Jan.25, 2005, and all the benefits accruing therefrom under 35 U.S.C. §119, the content of which in its entirety is herein incorporated by reference.

FIELD OF THE INVENTION

The present invention relates to a calibration apparatus for an optical scanner, a method of manufacturing the same, and a method of calibrating an optical scanner using the same.

DESCRIPTION OF THE RELATED ART

Various types of optical scanners, in particular, optical scanners for scanning arrays, are known in the art. The term "arrays" refer to assemblies of probes or binding agents that are spatially defined and arranged in a physically addressable manner. That is, the term "arrays" mean substrates carrying thereon a plurality of probes spatially fixedly arranged in various patterns. The probes may be proteins, nucleic acids, or polysaccharides.

Generally, an array optical scanner includes an optical source irradiating light onto a surface of an array and an optical detector detecting a detactable light (e.g., fluorescent light) emitted from the surface of the array. Representative examples of biopolymeric array optical scanners are disclosed in U.S. Pat. Nos. 5,585,639 and 6,258,593. Also, a microarray scanner, model G2565AA (Agilent Technology, Inc.) is commercially available.

As described above, an optical scanner suitable herein generally includes at least one optical source producing at least one coherent light beam of a specific wavelength, a scanning unit scanning the light beam over a surface of a substrate such as an array, and an optical detector detecting light (e.g., fluorescence) emitted from a sample region on the surface of the substrate.

Generally, the optical elements of the optical scanner are calibrated during manufacturing. Methods and apparatuses for calibrating an optical source are known (e.g., U.S. Pat. Nos. 5,464,960 and 5,772,656). However, a method of calibrating optical elements such as an optical detector after manufacturing an optical scanner is not so known. Thus, since easy, accurate, and inexpensive calibration devices for various optical elements including an optical detector are not currently available, periodic calibration of these devices is not done.

U.S. Pat. No. 6,794,424 discloses a novel calibration device that can be used as a standard device for calibrating an optical scanner, and a calibration method therefore. The calibration device includes a substrate on which a polymer layer including a fluorescent agent is formed. However, since illumination light must pass through the substrate and the polymer layer to reach the fluorescent agent, the substrate and the polymer layer should be made of a transparent material. Furthermore, the polymer layer must be uniformly coated on the transparent substrate, but a coating process such as spin coating is inappropriate for forming very thin and uniform films. Uniform dispersion of the fluorescent agent in the polymer layer is also difficult. In addition, the polymer layer must have an adhesive property to the substrate and be evenly and uniformly adhered to the substrate. When there are defects between the polymer layer and the substrate, nonuniform scan signals can be obtained.

A CyDye standard array manufactured by dissolving a fluorescent material called CyDye (Full Moon Biotechnology, Inc.) in a solvent and spotting the mixed solution onto a microarray is also known as a standard for optical scanner calibration. However, the CyDye standard array must be stored in a dark place because it is easily chemically decomposed, and a storage period is merely about one month.

In view of the problems of the above-described conventional techniques, a standard optical scanner calibration device that can be easily manufactured, has a long lifetime, and provides a stable fluorescence signal is still needed.

SUMMARY OF THE INVENTION

The present invention provides an optical scanner calibration apparatus which can be easily manufactured, has a long lifetime, and provides a stable fluorescence signal.

The present invention also provides a method of easily manufacturing the optical scanner calibration apparatus.

The present invention also provides a method of calibrating an optical scanner using the optical scanner calibration apparatus.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
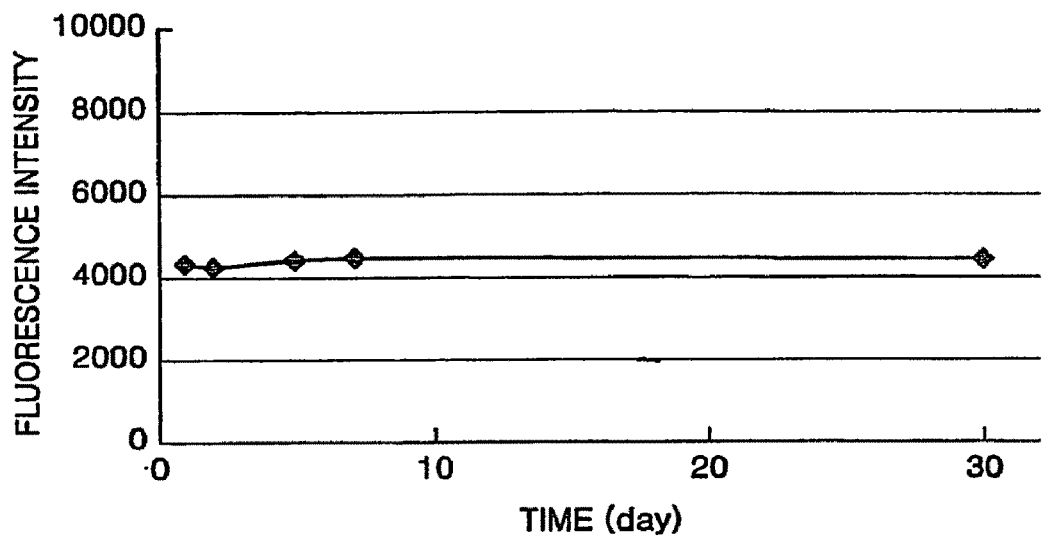
FIG. 1 is a view illustrating measurements of the intensity of fluorescence emitted from a substrate illuminated with illumination light at predetermined time intervals.

The present invention provides a calibration apparatus for an optical scanner, the apparatus including a substrate on which a molecule capable of forming an excimer is immobilized.

In the calibration apparatus of the present invention, the term "excimer" refers to a substance in which two or more atoms or molecules are joined in an excited state and the joined atoms or molecules are released or substantially released from each other in a ground state. The molecule capable of forming the excimer (hereinafter, simply referred to as "excimer-forming molecule") may be a fluorescent agent selected from pyrene, 2-phenylindole, and a derivative thereof, but the present invention is not limited thereto. The substrate is a transparent or opaque substrate and may be a solid material commonly known in the art. The substrate may be selected from the group consisting of a silicon wafer, a glass, and a plastic. The size, surface shape, and material of the substrate may vary according to an optical scanner to be used together with the substrate. The substrate may be flexible or hard. Examples of the flexible substrate include a membrane and a flexible plastic film. Both the flexible and hard substrates must provide a physical support and structure to manufacture a biopolymeric array thereon. The substrate may have various configurations. The thickness of a layer composed of the excimer-forming molecule formed on the substrate is not particularly limited, but may be a range from 1 to 100 Å.

Unlike the calibration device disclosed in U.S. Pat. No. 6,794,424, the calibration apparatus of the present invention can have a simple structure and a uniform molecule layer thickness since a polymer layer is not used and a fluorescent substance, i.e., the excimer-forming molecule is directly immobilized on the substrate or is immobilized on the substrate via a linker. The immobilization of the excimer-forming molecule on the substrate can be performed by a commonly known method for immobilization of a compound on a substrate. For example, the immobilization of the excimer-forming molecule can be done by coating a functional group such as an amino group on a substrate and reacting the functional group with an activated excimer-forming molecule. In more detail, an amino group of aminosilane such as 3-aminopropyltriethoxysilane is incorporated onto a surface of a solid support in a self-assembled manner. Then, a pyrene molecule containing a good leaving group such as succinimide ester as an excimer-forming molecule is allowed to react with the amino group-incorporated solid support to thereby immobilize the excimer-forming molecule on the substrate. The excimer-forming molecule must be immobilized so that a local and global fluorescence variation on the substrate is minimized, i.e., local and global nonuniformity is minimized. Generally, the local and global nonuniformity must be minimized to a degree sufficient to enable the calibration of a particular optical scanner adapted to the calibration apparatus of the present invention.

In the calibration apparatus of the present invention, the substrate may include a region that is outside of a calibration region, i.e., a background region, on which the excimer-forming molecule is not immobilized. The calibration apparatus of the present invention may generally include a plurality of background regions set on a surface of the apparatus.

The calibration apparatus of the present invention is used to calibrate an optical scanner, particularly a biopolymeric array optical scanner (hereinafter, simply referred to as "optical scanner"), and more particularly a biopolymeric array optical detector, lens, stage, and mirror. An optical scanner to be calibrated by the calibration apparatus of the present invention will now be described in brief.

Optical Scanner

Various types of optical scanners, in particular, optical scanners for scanning arrays, are known in the art. The term "arrays" refer to assemblies of probes or binding agents that are spatially defined and arranged in a physically addressable manner. That is, the term "arrays" mean substrates carrying thereon a plurality of probes spatially fixedly arranged in various patterns. The probes may be proteins, nucleic acids, or polysaccharides.

Generally, an array optical scanner includes an optical source irradiating light onto a surface of an array and an optical detector detecting a detactable light (e.g., fluorescent light) emitted from the surface of the array. Representative examples of biopolymeric array optical scanners are disclosed in U.S. Pat. Nos. 5,585,639 and 6,258,593, and a microarray scanner, model G2565AA (Agilent Technology, Inc.) is commercially available. However, the present invention is not limited thereto.

As described above, an optical scanner suitable herein generally includes at least one optical source producing at least one coherent light beam of a specific wavelength, a scanning unit scanning the light beam on a surface of a substrate such as an array, and an optical detector detecting light (e.g., fluorescence) emitted from a sample region on the surface of the substrate.

The optical source is generally an optical source capable of illuminating a surface of the substrate, e.g., a surface of an array, with light in a portion of the electromagnetic spectrum which can be detected by a photomultiplier tube (PMT) of the optical scanner. Occasionally, two or more optical sources or two or more wavelengths are used to illuminate a surface of a substrate. For example, a dual laser scanner may be used. The optical source may be a light-emitting diode, a laser diode, or a filtered lamp. A dye laser, a titanium sapphire laser, a Nd:YAG laser, an argon laser, or any other laser may be used in the laser optical source. The optical source may also include a scan lens system for focusing illumination light on desired-sized illumination areas of an array.

The scanning unit is generally associated with the optical source to scan or raster a light beam in one or more directions over a surface of a substrate. A suitable scanning unit includes a mirror, e.g., a scanner mirror, controlled by a motor such as a galvo-scanner motor. The scanning unit can move a light beam over a surface with a predetermined length.

The optical scanner also includes an optical detector capable of detecting visible light emitted from a substrate, e.g., fluorescent light. The optical detector may be a photodiode, a PMT, a photodetector, or a phototransistor, but the present invention is not limited thereto. An imaging lens system designed to image light emitted from a surface of a substrate in response to the optical source in an imaging plane alignable with the optical detector may be associated with the optical detector. The imaging lens system may include a filter for selectively blocking a light beam reflected from a surface of a substrate.

A microprocessor, which is operably linked at least to the scanner motor, controls the movement and position of the mirror and the optical detector to receive a digital or analogue signal related to a light emission level measured by the optical detector.

In a typical scanning procedure, when at least one illumination light beam is scanned across an array substrate, fluorescence is excited in each region of each scanned linear array where a fluorescence-labeled analyte is bound. The emitted light is imaged onto the detector and the intensity of the emitted light is measured. The measured intensity associated with each region of the array is recorded and stored, together with the associated region. After the array has been completely scanned, an output map showing a light intensity associated with each region of the array is typically automatically generated by the scanner. The output may include the identity of molecule species at which a fluorescence signal is observed or sequence information of the analyte.

The present invention also provides a method of manufacturing an optical scanner calibration apparatus, which includes reacting a substrate coated with a functional group and a molecule capable of forming an activated excimer to immobilize the molecule on the substrate.

In the manufacturing method of the present invention, examples of the functional group may include, but are not limited to, an amino group, a hydroxyl group, and a thiol group. The amino group may be derived from a compound selected from putrescine, spermidine, and spermine. The substrate coated with the functional group may be manufactured by a method known in the art. For example, a molecule containing the functional group may be spin-coated or dip-coated on a substrate or may be formed as a self-assembled monolayer on a substrate.

In the manufacturing method of the present invention, the molecule capable of forming the activated excimer is not particularly limited provided that it is an excimer-forming molecule coupled with a good leaving group. For example, pyrene, 2-phenylindole, or a derivative thereof, which is linked to N-hydroxysuccinimide (NHS) via an ether bond, may be used. However, the present invention is not limited thereto. For example, the molecule capable of forming the activated excimer may be a compound represented by formula 1 below:

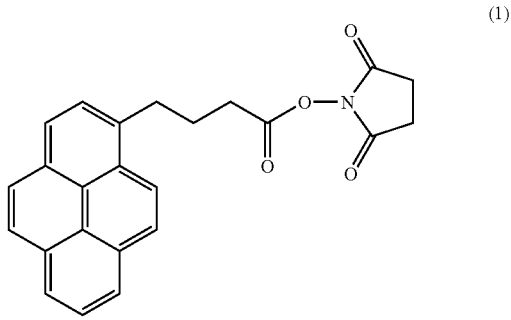

(1)

The reaction condition may vary according to the functional group on the substrate and the activated excimer-forming molecule selected. It should be understood that those of ordinary skill in the art could determine an optimal reaction condition.

The present invention also provides a method of calibrating an optical scanner, which includes: (a) illuminating a surface of an optical scanner calibration apparatus of the present invention with light emitted from at least one optical source; (b) obtaining fluorescence data from the surface of the calibration apparatus; and (c) calibrating the optical scanner based on the fluorescence data.

Generally, as described above, the surface of the calibration apparatus is illuminated with light from the at least one optical source, and the fluorescence data are obtained from the illuminated surface. Occasionally, the calibration apparatus of the present invention is disposed on a support stage or the like so that the substrate side on which an excimer-forming molecule is immobilized faces the optical source. However, when the substrate is made of a transparent material such as glass, the substrate side on which an excimer-forming molecule is immobilized does not necessarily face the optical source and the substrate side on which an excimer-forming molecule is immobilized may also face the oppositie direction of optical source, which is opposed to a conventional optical calibration apparatus. Based on the fluorescence data, the optical scanner is confirmed (i.e., no adjustments are made), or adjusted or calibrated. Here, the "adjusted or calibrated" means that at least one of the following is adjusted: (1) scale factor (i.e., the sensitivity of an optical detector), (2) focus position (i.e., the distance between a stage and at least one lens of a scanner), and (3) dynamic focus (i.e., a movement speed of a stage), where each of these will be described in detail below.

1. Scale Factor Calibration

Fluorescence data from the calibration apparatus of the present invention can be used to verify the scale factor of an optical scanner, i.e., the sensitivity of a detector of the optical scanner, and, if necessary, to calibrate or adjust the sensitivity of the detector.

After the calibration apparatus of the present invention is scanned as described above, an empirical calibration value defined as the number of photons in a pixel over fluorophores per $\mu m^2$ is calculated based on the intensity of a fluorescence signal. Thus, current corresponding to the intensity of light emitted per pixel is converted to digital counts which are used to determine a calibration value for each optical detector. The empirically derived calibration value and corresponding digital signal are then compared to a standard calibration value/signal function. That is, the empirically derived calibration value/signal is compared to a standard value that is a function dependent on the specific fluorescent substance used, the type of optical detector employed, the area of the pixel, etc. The optical scanner is adjusted in response to the comparison. The standard values obtained from a single calibration apparatus can be used to calibrate a plurality of optical scanners in parallel.

In more detail, a detector such as a PMT is used to detect the intensity of the light emitted from a single fluorophore, generally, the intensity of the light in the form of a voltage measurement. Such intensity is relayed to a microprocessor via a software program, i.e., a microprocessor operably linked to an optical scanner including the detector, and carries out all the operations necessary to determine if the detector characteristics are within specified ranges or need to be adjusted. The microprocessor can also perform operations necessary to adjust the detector.

In a case where the sensitivity of the detector is given by a voltage, the detector is calibrated or adjusted by altering the voltage of the detector. That is, an empirical calibration value, i.e., the signal from the PMT operated at a known voltage is obtained, and then compared to a standard value. If the voltage related to the empirical calibration value is different from a standard voltage, the sensitivity or voltage of the detector is altered to change the response of the detector.

2. Focus Position Calibration

The present invention provides a method of calibrating or adjusting at least one scanning stage (i.e., the distance between the scanning stage and an optical lens) of an optical scanner. According to the method, the focus position of a laser relative to the surface of a scanned object can be adjusted to optimize the intensity of the light detected.

First, as described above, the calibration apparatus of the present invention is scanned with at least one optical source at various depths. That is, a light beam scans a surface of the calibration apparatus of the present invention where a number of different focal positions are used to scan the surface. After specific areas of the surface of the calibration apparatus of the present invention are scanned at various depths, a focal position providing an optimal signal is selected, and the distance between the optical or focusing lens and the scanning stage is adjusted or calibrated to provide the optimal focal depth. The focal distance is then stored in a microprocessor operably linked to the optical scanner so that the optical scanner performs scanning at the focal distance later. That is, an optimal focus depth is determined based on the above scan, and the distance between the stage and lens is adjusted by adjusting the position of the scanning stage to correspond to the optimal configuration to provide the optimal scanning depth for subsequence scans.

3. Dynamic Focus Calibration

The present invention also provides a method of adjusting the movement speed of an optical stage of an optical scanner on which a scanned object such as a biopolymeric array is placed during a scanning procedure. The stage aligns the scanned object in a certain position to correspond to a scanning light beam. That is, in use, the stage is moved to align an optical scanner to correspond to an area of the scanned object such as a certain linear array area on a substrate. The focus of the optical scanner may vary according to parameters related to the optical stage such as the movement speed of the stage. For example, if the stage moves too quickly or is out of alignment, the scan will be out of the focus.

First, as described above, a series of horizontal scan lines or planes of a surface of the calibration apparatus of the present invention are scanned by at least one optical source. Then, the oscillation of the detected intensity image of these scanned horizontal planes is measured. If the oscillation is within a specific value range, the movement speed of the stage increases or decreases to optimize the focus of the optical scanner. The increased or decreased movement speed of the stage is stored in a microprocessor operably linked to the optical scanner so as to be used for subsequent scans.

Thus, in the calibration method of the present invention, the operation of illuminating may include illuminating the surface of the calibration apparatus with light in a portion of electromagnetic spectrum which can be detected by a PMT of the optical scanner. The illuminated light may be light in a wavelength range selected from the group consisting of ultraviolet, visible, and infrared.

In the calibration method of the present invention, the operation of obtaining the fluorescence data may include detecting a signal related to the intensity of the light emitted from the excimer-forming molecule.

In the calibration method of the present invention, the operation of calibrating may include calibrating the scale factor of the optical scanner. Specifically, the scale factor calibration may include adjusting the sensitivity of an optical detector of the optical scanner. The operation of calibrating may also include calibrating the focal position of the optical scanner. For example, the focal position calibration may include adjusting the distance between a scanning stage and a lens of the optical scanner. The operation of calibrating may also include calibrating the dynamic focus of the optical scanner. For example, the dynamic focus calibration may include adjusting the movement speed of an optical stage of the optical scanner. The operation of calibrating may also include determining the amount of oscillation in an intensity image and adjusting the movement speed of the optical stage according to the oscillation data.

The calibration method of the present invention may also include subtracting a background signal from the obtained fluorescent data to obtain a background corrected value.

Hereinafter, the present invention will be described more specifically with reference to the following examples. The following examples are for illustrative purposes and are not intended to limit the scope of the invention.

EXAMPLES

Example 1

Manufacturing of Pyrene-Immobilized Substrate

In this Example, a compound represented by formula 1 (1-pyrenebutyric acid γ-hydroxysuccinimide ester) was allowed to react with an amino group-activated substrate to immobilize pyrene molecules on the substrate, thereby obtaining a pyrene-immobilized substrate.

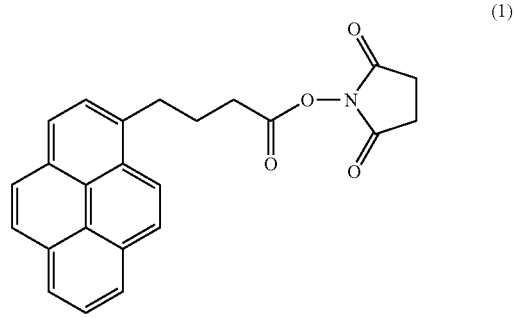

(1)

A silicon substrate having a SiO$_2$ layer with a thickness of 1,000 Å was used as the amino group-activated substrate. The silicon substrate was treated with γ-aminopropyltriethoxy silane (GAPS) as a coupling agent to attach an amino group to the silicon substrate, followed by intercalator incorporation.

(1) Treatment of Silicon Substrate with Coupling Agent (GAPS)

Prior to surface treatment, a silicon substrate was carefully cleaned with pure acetone and water, and an organic contaminant was then removed from the silicon substrate using a piranha solution composed of hydrogen peroxide and sulfuric acid (1:3). Finally, the silicon substrate was washed with a large quantity of water and acetone and dried. Here, the cleaning procedure was performed in a wet station used in a semiconductor fabrication process, a sulfuric acid bath was used for the piranha solution, and the washing procedure with water was performed by a QDR process. The silicon substrate was fixed on a silicon wafer carrier made of Teflon and then cleaned. After the cleaning, the silicon substrate was dried using a spin drier.

Immediately after the cleaning, a solution of GAPS in ethanol (20%, v/v) was spin-coated on the silicon substrate. The spin coating was performed using a spin coater (model CEE 70, CEE). The spin coating was divided into initial coating at a rate of 500 rpm/10 sec and main coating at a rate of 2,000 rpm/10 sec. After the spin coating was completed, the silicon substrate was fixed on a Teflon wafer carrier and cured at 120° C. for 40 minutes. The cured substrate was dipped in water for 10 minutes, ultrasonically washed for 15 minutes, again dipped in water for 10 minutes, and dried. The drying was performed using a spin drier. The dried substrate was cut into square or rectangular pieces for experiments. All experiments were performed in a clean room-class 1000 in which most dust particles were sufficiently removed.

(2) Immobilization of Pyrene Molecules

A compound represented by formula 1 (1-pyrenebutyric acid ɤ-hydroxysuccinimide ester) was dip-coated on the silanized substrate obtained in (1). First, 1-pyrenebutyric acid ɤ-hydroxysuccinimide ester was dissolved in a methylenechloride solution to prepare a dipping solution (0.5 g of 1-pyrenebutyric acid ɤ-hydroxysuccinimide ester/200 ml+0.1 ml of triethylamine). The dipping solution and the silanized substrate were placed in a reactor and incubated at room temperature for 5 hours. After the reaction was terminated, the substrate was removed from the dipping solution and then cleaned with methylenechloride (×3, 10 minutes for each) and ethanol (×3, 10 minutes for each). The cleaned substrate was dried and the amount of 1-pyrenebutyric acid ɤ-hydroxysuccinimide ester was measured using GenePix 4000B fluorescence scanner (Axon). Light at 532 nm was scanned, and fluorescence intensity was measured at 570 nm.

Example 2

Fluorescence Emission Characteristics of Pyrene-Immobilized Substrate

The characteristics of the pyrene-immobilized substrate manufactured in Example 1 were evaluated.

(1) Durability Test

The degree of the fluorescence emission from the substrate with time was measured.

First, the substrate manufactured in Example 1 was left in an ambient condition. The substrate was illuminated with illumination light at predetermined time intervals and the intensity of fluorescence emitted from the substrate was measured.

FIG. 1 is a view illustrating measurements of the intensity of fluorescence emitted from a substrate illuminated with illumination light at predetermined time intervals. As shown in FIG. 1, the fluorescence intensity was very stably changed within a dispersion value of 3 to 5% during about 30 days.

Next, the fluorescence emission characteristics of the substrate manufactured in Example 1 in a severe condition were evaluated. For this, excitation light was continuously irradiated 100 times on the substrate manufactured in Example 1 and the intensity of fluorescence emitted from the substrate was measured. The substrate was left for one day after the 100-th fluorescence measurement was completed, and then a 101-th fluorescence measurement was performed.

Figure 2:
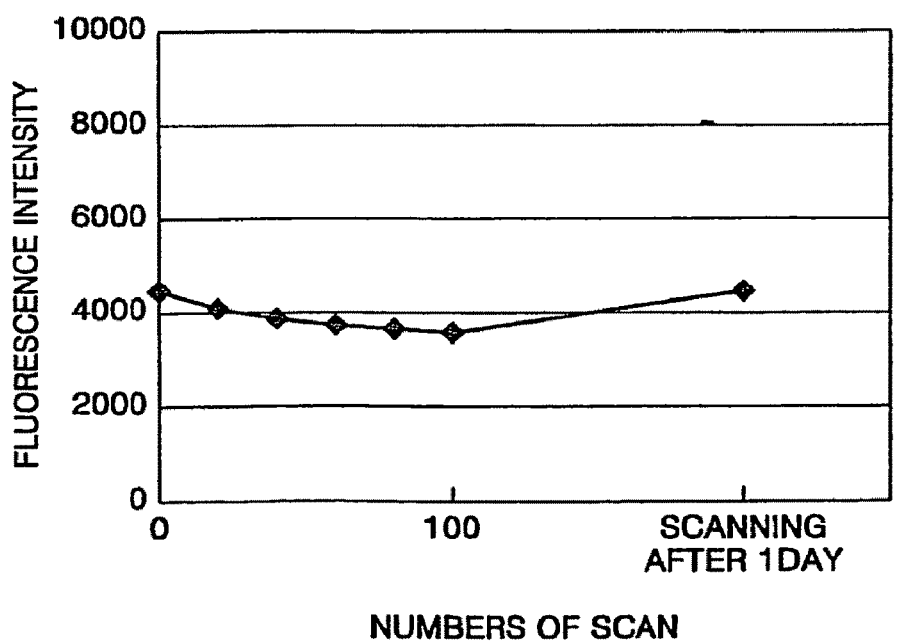
FIG. 2 is a view illustrating continuous fluorescence measurements for a substrate manufactured in Example 1.

FIG. 2 is a view illustrating continuous fluorescence measurements for a substrate manufactured in Example 1. As shown in FIG. 2, when excitation light was continuously irradiated, the intensity of fluorescence emitted was reduced. However, at about one day after the continuous irradiation, the intensity of fluorescence emitted was recovered to an original level.

From the results of FIG. 2, it can be seen that fluorescence emission characteristics are recovered at a predetermined time after the irradiation of excitation light onto the substrate manufactured in Example 1. To determine the recovery time of the fluorescence emission characteristics after excitation light irradiation, the intensity of fluorescence with time after excitation light irradiation was measured.

Figure 3:
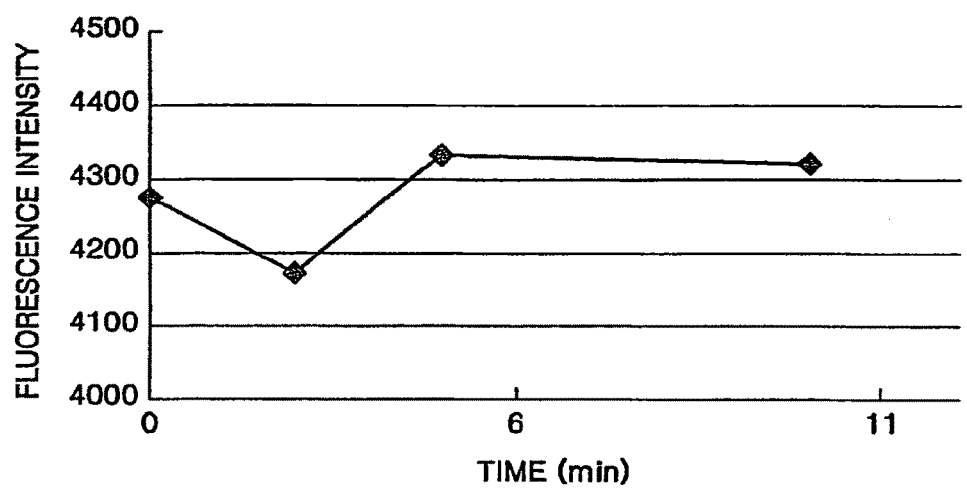
FIG. 3 is a view illustrating the recovery of fluorescence emission characteristics after excitation light is 20 times irradiated onto the substrate manufactured in Example 1.

FIG. 3 is a view illustrating the recovery of fluorescence emission characteristics after excitation light is irradiated 20 times onto the substrate manufactured in Example 1. Referring to FIG. 3, the fluorescence emission characteristics were recovered at about 5 minutes after the 20 times excitation light irradiation.

Example 3

Sensitivity Calibration Using the Substrate Manufactured in Example 1

The substrate manufactured in Example 1 was used as a calibration standard, and scanning was performed over a PMT range of 200-700 using Axon 1 and Axon 2 (Genepix 4000B model, Axon) to obtain fluorescence data. Then, experimental fluorescence intensity with respect to the PMT value was calculated. A scanning wavelength was 532 nm. Scanning was performed while increasing the PMT value from 200 to 700. As the PMT value increased, the intensity of the fluorescence increased rapidly. Each scan area was adjusted to 2-5 mm$^2$ (확인요).

Figure 4:
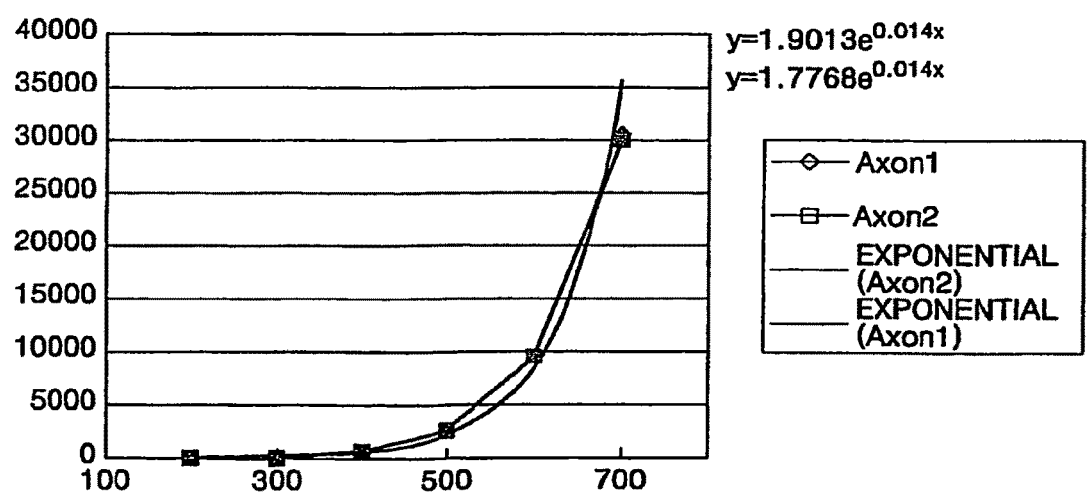
FIG. 4 is a view illustrating fluorescence data after scanning the substrate manufactured in Example 1 as a calibration standard over a PMT range of 200-700 using Axon 1 and Axon 2 (Genepix 4000B model, Axon)

FIG. 4 is a view illustrating fluorescence data after scanning the substrate manufactured in Example 1 as a calibration standard over a PMT range of 200-700 using Axon 1 and Axon 2 (Genepix 4000B model, Axon). Assuming that the PMT value was x and the fluorescence intensity measured was y, the function values for Axon 1 and Axon 2 were represented by $y=1.9013e^{0.014x}$ and $y=1.7768e^{0.014x}$, respectively.

Next, whether or not scanner calibration was possible was determined using the experimental function values thus obtained. When the fluorescence intensity with respect to the substrate was 5,000, the PMT values of Axon1 and Axon2 were calculated as 562 and 567, respectively. Fluorescence intensity was measured after scanning the substrate manufactured in Example 1 over PMT values of 562 and 567 for Axon1 and Axon2, respectively.

Figure 5A:
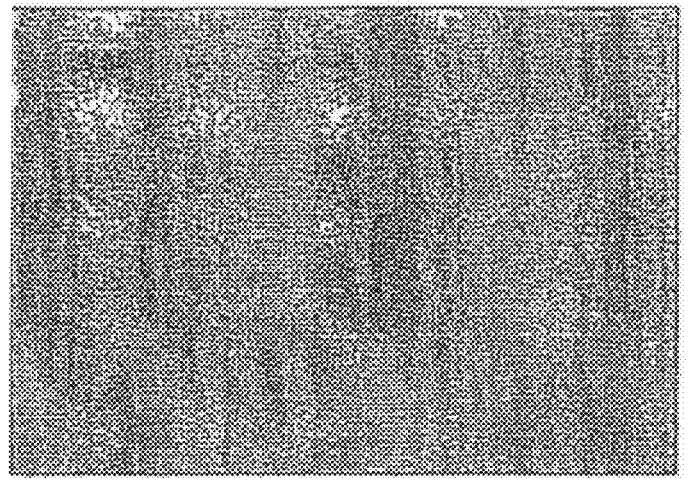
FIG. 5 is a view illustrating fluorescence measurements after scanning the substrate manufactured in Example 1 over a PMT range of 562 and 567 for Axon1 and Axon2, respectively.
Figure 5B:
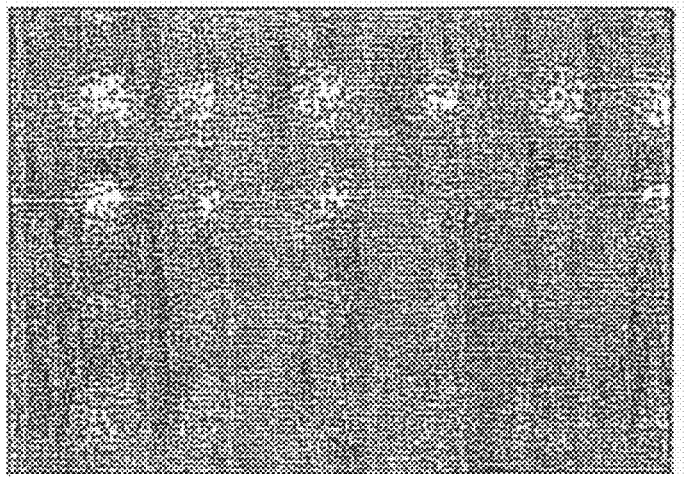

FIG. 5 is a view illustrating fluorescence measurements after scanning the substrate manufactured in Example 1 over PMT values of 562 and 567 for Axon1 and Axon2, respectively. As shown in FIG. 5, the fluorescence intensities for Axon 1 and Axon2 were 5861 (A) and 5801 (B), respectively. A deviation between the two scanners was within 1%. This shows that the substrate manufactured in Example 1 is suitable to be used in sensitivity calibration.

The calibration apparatus of the present invention has good durability and can repeatedly scan fluorescence.

According to the method of manufacturing the calibration apparatus of the present invention, the calibration apparatus can be easily manufactured.

According to the method of calibrating an optical scanner of the present invention, an optical scanner can be repeatedly calibrated by the same calibration apparatus with a long lifetime.

What is claimed is:

1. A method of manufacturing a calibration apparatus for an optical scanner, the method comprising:

reacting a substrate coated with a functional group and a molecule capable of forming an activated excimer to immobilize the molecule on the substrate, wherein the functional group is an amino group derived from a compound selected from the group consisting of γ-aminopropyltriethoxysilane, putrescine, spermidine, and spermine.

2. The method of claim 1, wherein the molecule is a compound represented by formula 1 below:

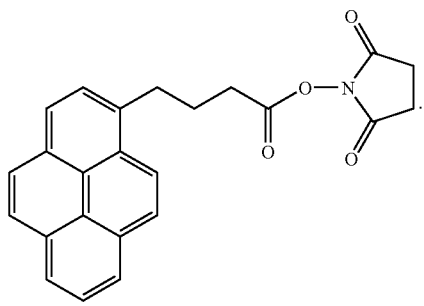

(1)

3. A method of manufacturing a calibration apparatus for an optical scanner, the method comprising:
reacting a substrate coated with a functional group and a molecule capable of forming an activated excimer to immobilize the molecule on the substrate, wherein the molecule is a compound represented by formula 1 below:

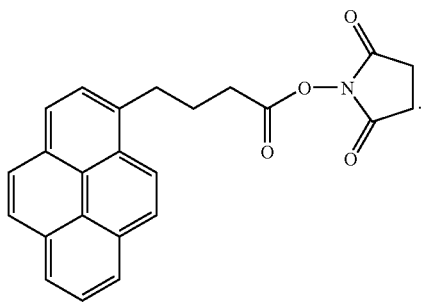

(1)

4. The method of claim 3, wherein the functional group is an amino group derived from a compound selected from the group consisting of γ-aminopropyltriethoxysilane, putrescine, spermidine, and spermine.

* * * * *